United States Patent
Ludescher et al.

(10) Patent No.: US 8,455,639 B2
(45) Date of Patent: Jun. 4, 2013

(54) CRYSTALLINE FORM OF AN ORGANIC COMPOUND

(75) Inventors: Johannes Ludescher, Kundl (AT); Josef Wieser, Kundl (AT); Gerhard Laus, Innsbruck (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 13/139,863

(22) PCT Filed: Dec. 18, 2009

(86) PCT No.: PCT/EP2009/067548
§ 371 (c)(1),
(2), (4) Date: Aug. 25, 2011

(87) PCT Pub. No.: WO2010/072680
PCT Pub. Date: Jul. 1, 2010

(65) Prior Publication Data
US 2011/0306764 A1    Dec. 15, 2011

(30) Foreign Application Priority Data
Dec. 23, 2008   (EP) .................................... 08172772

(51) Int. Cl.
*C07D 239/10*    (2006.01)

(52) U.S. Cl.
USPC ........................................... 544/309; 544/312

(58) Field of Classification Search
USPC .................................................... 544/312, 309
See application file for complete search history.

(56) References Cited

FOREIGN PATENT DOCUMENTS

| WO | 2005095381 A1 | 10/2005 |
| WO | 2007035372 A2 | 3/2007 |
| WO | 2007035629 A2 | 3/2007 |

OTHER PUBLICATIONS

International Search Report and Written Opinion (mailed Feb. 2, 2010).
Feng, Zhiyuan Zhang, Michael B. Wallace, Stephen L. Gwaltney et al. in J.Med. Chem. 2007, 50, 2297; or Drugs of the Future 2008, 33, 7.

*Primary Examiner* — Wu-Cheng Winston Shen
*Assistant Examiner* — Karen Cheng
(74) *Attorney, Agent, or Firm* — Jeffrey S. Melcher; Manelli Selter PLLC

(57) ABSTRACT

The present invention is directed to a crystalline form of 2-[6-[3(R)-aminopiperidin-1-yl]-3-methyl-2,4-dioxo-1,2,3,4-tetrahydropyrimidin-1-ylmethyl]-benzonitrile, a process for the preparation of said crystalline form and the use thereof in the manufacture of a pharmaceutical composition.

5 Claims, 2 Drawing Sheets

CRYSTALLINE FORM OF AN ORGANIC COMPOUND

CROSS-REFERENCE TO RELATED APPLICATIONS

This application is a national stage entry under 35 U.S.C. 371 of International Application No. PCT/EP2009/067548, filed 18 Dec. 2009, designating the U.S. This application claims foreign priority under 35 U.S.C. 119 and 365 to European Patent Application No. 08172772.9, filed 23 Dec. 2008. The complete contents of these applications are incorporated herein by reference.

FIELD OF THE INVENTION

The present invention relates to a crystalline form of 2-[6-[3(R)-aminopiperidin-1-yl]-3-methyl-2,4-dioxo-1,2,3,4-tetrahydropyrimidin-1-ylmethyl]-benzonitrile, a process for the preparation of said crystalline form and the use of said crystalline form in the manufacture of a pharmaceutical composition.

BACKGROUND OF THE INVENTION

Alogliptin or 2-[6-[3(R)-aminopiperidin-1-yl]-3-methyl-2,4-dioxo-1,2,3,4-tetrahydropyrimidin-1-ylmethyl]-benzonitrile has the general formula (A) as shown below and is a DPP-IV inhibitor currently in development for use for the treatment of a disease state for which an DPP-IV inhibitor possesses activity, e.g. for the treatment of diabetes as disclosed by Jun Feng, Zhiyuan Zhang, Michael B. Wallace, Stephen L. Gwaltney et al. in J. Med. Chem. 2007, 50, 2297 ff or Drugs of the Future 2008, 33, 7 ff. The marketed form is intended to be the benzoate salt of 2-[6-[3(R)-aminopiperidin-1-yl]-3-methyl-2,4-dioxo-1,2,3,4-tetrahydropyrimidin-1-ylmethyl]-benzonitrile, 2-[6-[3(R)-aminopiperidin-1-yl]-3-methyl-2,4-dioxo-3,4-dihydro-2H-pyrimidin-1-ylmethyl]-benzonitrile benzoate.

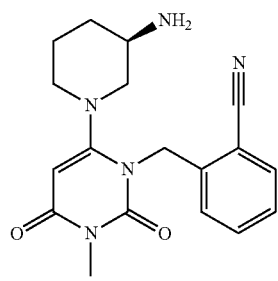

(A)

The preparation of alogliptin is disclosed for example in WO 2005/095381 and WO 2007/035629. WO 2007/035372 discloses an amorphous form and a crystalline polymorph of alogliptin benzoate. According to WO 2005/095381 an off white powder of what is presumably the TFA salt of 2-[6-[3(R)-aminopiperidin-1-yl]-3-methyl-2,4-dioxo-1,2,3,4-tetrahydropyrimidin-1-ylmethyl]-benzonitrile is obtained from the reaction mixture.

A crystalline form of 2-[6-[3(R)-Aminopiperidin-1-yl]-3-methyl-2,4-dioxo-1,2,3,4-tetrahydropyrimidin-1-ylmethyl]-benzonitrile has not been available according to the cited literature.

Polymorphism is a phenomenon relating to the occurrence of different crystal forms for one molecule. There may be several different crystalline forms for the same molecule with distinct crystal structures and varying in physical properties like melting point, XRPD spectrum and IR-spectrum. These polymorphs are thus distinct solid forms which share the molecular formula of the compound from which the crystals are made up, however they may have distinct advantageous physical properties which can have a direct effect on the ability to process and/or manufacture the drug substance, like e.g. flowability, and the drug product, like e.g. flowability, as well as on drug product stability, dissolution properties, and bioavailability.

According to the state of the art, e. g. WO 2007/035629, 2-[6-[3(R)-aminopiperidin-1-yl]-3-methyl-2,4-dioxo-1,2,3,4-tetrahydropyrimidin-1-ylmethyl]-benzonitrile is preferably isolated as an addition salt following the synthesis method starting from 2-(6-chloro-3-methyl-2,4-dioxo-3,4-dihydro-2-H-pyrimidin-1-ylmethyl)benzonitrile and (R)-3-amino-piperidine dihydrochloride, e.g. as hydrochloride, benzoate, trifluoroacetate or tosylate. The described preparation methods generally lead to production of a dimeric byproduct of general formula (B) which is difficult to remove from the desired product.

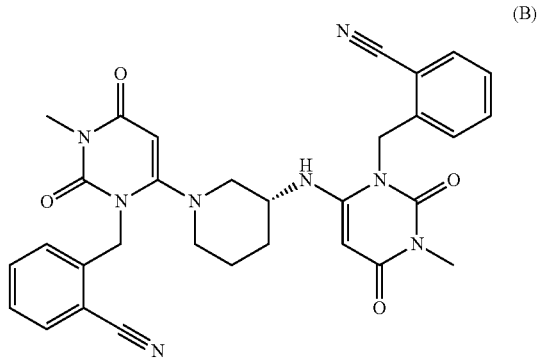

(B)

There is thus a need for improved processes for the production of 2-[6-[3(R)-aminopiperidin-1-yl]-3-methyl-2,4-dioxo-1,2,3,4-tetrahydropyrimidin-1-ylmethyl]-benzonitrile acid addition salts, in particular processes which efficiently remove the dimeric byproduct of general formula (B) while at the same time being suitable for large scale production at low cost.

SUMMARY OF THE INVENTION

The present invention is directed to a crystalline form of alogliptin in the form of the free base.

In one embodiment the present invention refers to a crystalline form of 2-[6-[3(R)-aminopiperidin-1-yl]-3-methyl-2,4-dioxo-1,2,3,4-tetrahydropyrimidin-1-ylmethyl]-benzonitrile.

In a preferred embodiment, the invention relates to crystalline 2-[6-[3(R)-aminopiperidin-1-yl]-3-methyl-2,4-dioxo-1,2,3,4-tetrahydropyrimidin-1-ylmethyl]-benzonitrile, wherein the x-ray powder diffraction comprises peaks at 2-theta of 10.9°±0.2°, 12.5°±0.2°, 18.0±0.2°, 19.0°±0.2°, 21.8°±0.2° and/or wherein the infrared spectrum shows peaks at 3358.7+/−2 cm$^{-1}$, 2223.7+/−2 cm$^{-1}$, 1642.2+/−2 cm$^{-1}$, 1433.4+/−2 cm$^{-1}$, 818.4+/−2 cm$^{-1}$ and 771.2+/−2 cm$^{-1}$.

In another embodiment the present invention refers to a process for the preparation of crystalline 2-[6-[3(R)-aminopiperidin-1-yl]-3-methyl-2,4-dioxo-1,2,3,4-tetrahydropyrimidin-1-ylmethyl]-benzonitrile comprising the steps of
a) providing a solution of 2-[6-[3(R)-aminopiperidin-1-yl]-3-methyl-2,4-dioxo-1,2,3,4-tetrahydropyrimidin-1-ylmethyl]-benzonitrile in a suitable chlorinated hydrocarbon, wherein the concentration of 2-[6-[3(R)-aminopiperidin-1-yl]-3-methyl-2,4-dioxo-1,2,3,4-tetrahydropyrimidin-1-ylmethyl]-benzonitrile is sufficiently high to allow crystallization of 2-[6-[3(R)-aminopiperidin-1-yl]-3-methyl-2,4-dioxo-1,2,3,4-tetrahydropyrimidin-1-ylmethyl]-benzonitrile;
b) adding an ether, a aliphatic or aromatic hydrocarbon as an antisolvent in an amount sufficient and at a rate suitable to cause crystallization of 2-[6-[3(R)-aminopiperidin-1-yl]-3-methyl-2,4-dioxo-1,2,3,4-tetrahydropyrimidin-1-ylmethyl]-benzonitrile from the solution of step a); and
c) isolating the crystalline form of 2-[6-[3(R)-aminopiperidin-1-yl]-3-methyl-2,4-dioxo-1,2,3,4-tetrahydropyrimidin-1-ylmethyl]-benzonitrile.

Furthermore, the present invention relates to the use of a crystalline form of 2-[6-[3(R)-aminopiperidin-1-yl]-3-methyl-2,4-dioxo-1,2,3,4-tetrahydropyrimidin-1-ylmethyl]-benzonitrile according to any of claims 1 to 6 in the manufacture of an acid addition salt of 2-[6-[3(R)-aminopiperidin-1-yl]-3-methyl-2,4-dioxo-1,2,3,4-tetrahydropyrimidin-1-ylmethyl]-benzonitrile containing less than 0.1% of dimeric impurity of general formula (B).

In a further embodiment, the present invention relates to 2-[6-[3(R)-Aminopiperidin-1-yl]-3-methyl-2,4-dioxo-1,2,3,4-tetrahydropyrimidin-1-ylmethyl]-benzonitrile benzoate containing less than 0.1% of dimeric impurity of general formula (B).

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the scope of the disclosed invention will become readily apparent to those skilled in the art from reading the description and from reading the other parts of the present disclosure.

DETAILED DESCRIPTION OF THE INVENTION

Figure 1:
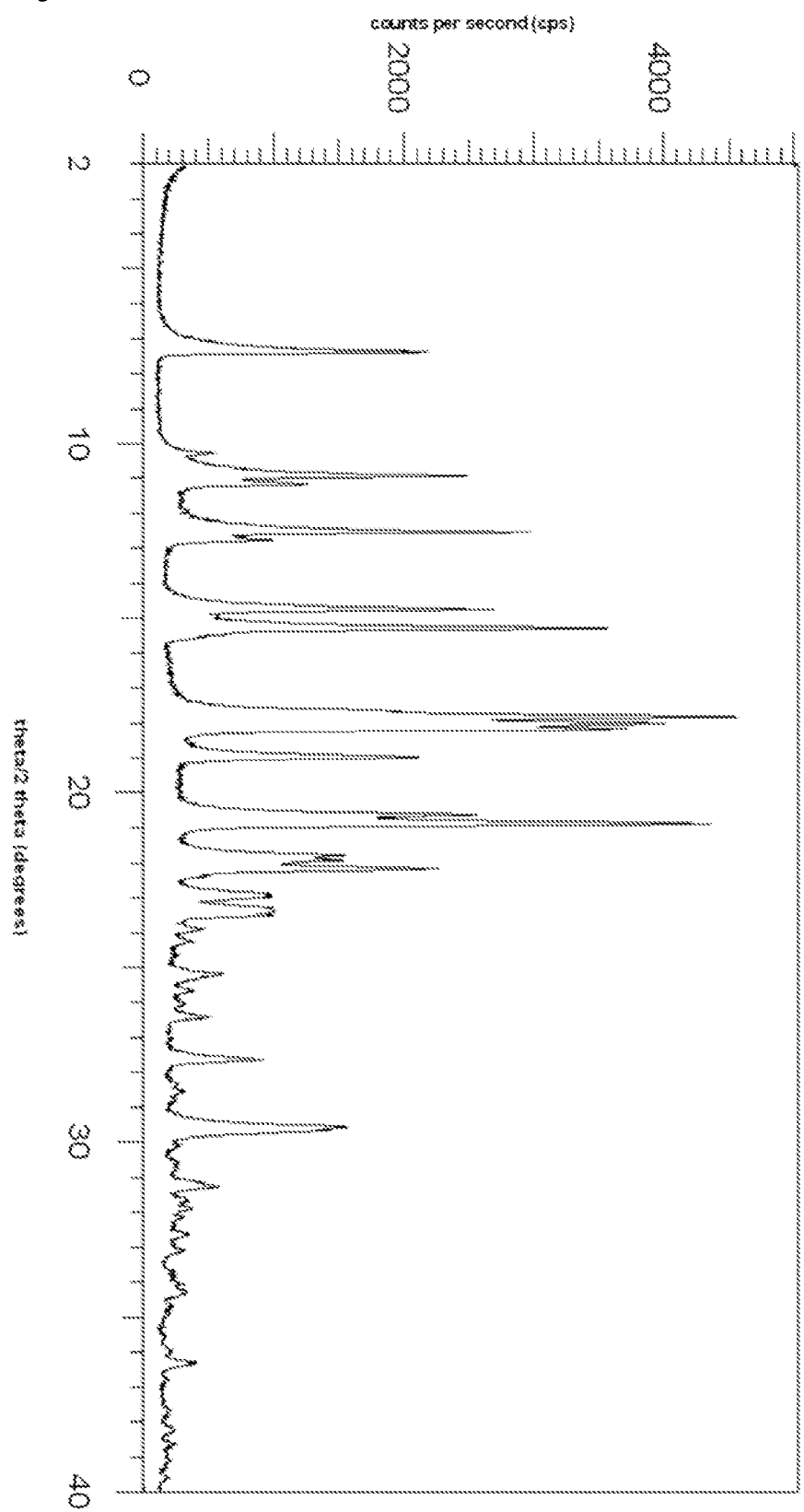
FIG. 1: X-ray powder diffraction pattern of crystalline alogliptin free base (2-[6-[3(R)-aminopiperidin-1-yl]-3-methyl-2,4-dioxo-1,2,3,4-tetrahydropyrimidin-1-ylmethyl]-benzonitrile) obtained from example 1.

The present invention relates to 2-[6-[3(R)-aminopiperidin-1-yl]-3-methyl-2,4-dioxo-1,2,3,4-tetrahydropyrimidin-1-ylmethyl]-benzonitrile in crystalline form.

The present inventors have surprisingly discovered and identified crystalline alogliptin free base and have found out that it is stable upon storage and that it is a very useful tool to remove certain impurities from alogliptin. These properties are important and prove advantageous for the desired use of addition salts of alogliptin free base in pharmaceutical formulations and for their preparation on an industrial scale.

Alogliptin or 2-[6-[3(R)-aminopiperidin-1-yl]-3-methyl-2,4-dioxo-1,2,3,4-tetrahydropyrimidin-1-ylmethyl]-benzonitrile has the general formula (A):

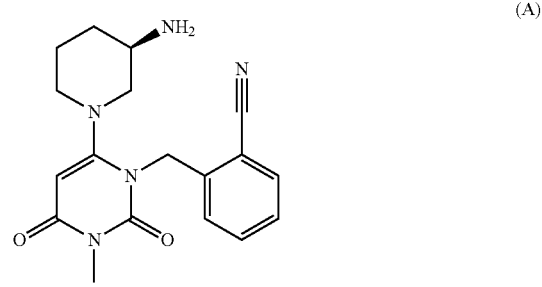

(A)

The present invention relates to crystalline 2-[6-[3(R)-aminopiperidin-1-yl]-3-methyl-2,4-dioxo-1,2,3,4-tetrahydropyrimidin-1-ylmethyl]-benzonitrile, in particular wherein the crystalline form is in anhydrous form.

In the context of the present invention, "anhydrous form" in particular means a form containing less than 1.6% of water when stored at 25° C. and 90% relative humidity. Therefore, according to a further embodiment, the present invention relates to the crystalline form of 2-[6-[3(R)-aminopiperidin-1-yl]-3-methyl-2,4-dioxo-1,2,3,4-tetrahydropyrimidin-1-ylmethyl]-benzonitrile as disclosed above, wherein the crystalline form is an anhydrous form containing less than 1.6% of water when stored at 25° C. and 90% relative humidity.

We have surprisingly found that the crystalline form of 2-[6-[3(R)-aminopiperidin-1-yl]-3-methyl-2,4-dioxo-1,2,3,4-tetrahydropyrimidin-1-ylmethyl]-benzonitrile of the invention is of low hygroscopicity, e.g. non hygroscopic, and very suitable for storage. It has been observed that upon storage the formation of undesired by— or degradation products which—without wishing to be bound by any theory—are thought to be caused in part by water uptake, can be avoided.

The crystalline form of 2-[6-[3(R)-aminopiperidin-1-yl]-3-methyl-2,4-dioxo-1,2,3,4-tetrahydropyrimidin-1-ylmethyl]-benzonitrile of the present invention is of low hygroscopicity, e.g. water uptake when stored about 25° C. for 60 min at a relative humidity of 50% of only about 0.4% w/w is observed, water uptake of only about 1.6% w/w is found when the crystalline base is stored at about 90% relative humidity at about 25° C. for 60 min. In these experiments humidity was increased/decreased stepwise. Starting at 0% relative humidity every one hour the humidity level was increased by 10% relative humidity. The gain/loss of weight was recorded continuously. The values given represent the value at the end of the one hour storage period at the indicated relative humidity level.

This water is easily lost, e.g. by storage at a relative humidity of 60% or less. No change in crystal structure nor the formation of a hydrated form is observed when exposing 2-[6-[3(R)-aminopiperidin-1-yl]-3-methyl-2,4-dioxo-1,2,3,4-tetrahydropyrimidin-1-ylmethyl]-benzonitrile to extremely high relative humidity.

The crystalline alogliptin free base of the invention thus offers the possibility of isolating the compound of general formula (A) in a technically very favorable manner and lends itself as a suitable form for storage and shipment. The invention therefore also relates to the use of the crystalline alogliptin free base of the invention as a storage- or shipment-form of alogliptin.

The present invention also relates to a storage container filled with commercial-scale batches of the crystalline alogliptin free base of the invention. According to the present invention, any suitable storage container can be used, for example boxes or bags. Commercial-scale batches can range from 1 g to 100 kg, in particular 5 g to 50 kg, in particular from 10 g to 20 kg of the crystalline alogliptin free base of the invention. The invention therefore also relates to storage bags filled with commercial-scale batches of the crystalline alogliptin free base of the invention, for example plastic or aluminum bags filled with from 5 g to 50 kg, in particular from 10 g to 20 kg of the crystalline alogliptin free base of the invention. The invention also relates to a storage pallet, e.g. a Euro-pallet, loaded with storage containers, in particular storage bags of the invention.

The crystalline alogliptin free base of the invention is freely flowable and easily isolated e.g. by filtration. A majority of the crystals is of a particle size of about 4 to 30 μm, e.g of about 10 to 30 μm when examined under a microscope.

It is a further advantage of the present invention that isolation of the basic intermediate of general formula (A) allows a simpler process for the production of highly pure 2-[6-[3(R)-aminopiperidin-1-yl]-3-methyl-2,4-dioxo-1,2,3,4-tetrahydropyrimidin-1-ylmethyl]-benzonitrile or an acid addition salt thereof, like the benzoate, than the prior art process of first producing a first salt, e.g. a hydrochloride salt—with corrosive properties—or e.g. a trifluoroacetate salt—an environmentally non acceptable chemical species, followed by conversion of the first isolated salt into the final salt intended to be used as drug product, and that this production proceeds without the need to employ procedures which are cumbersome on an industrial scale, such as column chromatography.

Furthermore crystalline 2-[6-[3(R)-aminopiperidin-1-yl]-3-methyl-2,4-dioxo-1,2,3,4-tetrahydropyrimidin-1-ylmethyl]-benzonitrile is chemically stable, e.g. at ambient temperature or below, e.g. samples stored for 4 months at ambient temperature show no degradation when measured e.g. by HPLC.

The novel crystalline alogliptine free base of the invention may be characterized e.g. by a typical X-ray powder diffraction pattern, an infrared spectrum or a melting point. Each of these characteristics on its own is sufficient to unambiguously define and identify the crystalline form of alogliptin free base but they also may be combined with each other.

Therefore, according to a further embodiment, the present invention is directed to the crystalline form of 2-[6-[3(R)-aminopiperidin-1-yl]-3-methyl-2,4-dioxo-1,2,3,4-tetrahydropyrimidin-1-ylmethyl]-benzonitrile as disclosed above, wherein the x-ray powder diffraction comprises peaks at 2-theta of 10.9°±0.2°, 12.5°±0.2°, 18.0±0.2°, 19.0°±0.2°, 21.8°±0.2°.

The x-ray powder diffraction diagram of to the preferred crystalline form of 2-[6-[3(R)-aminopiperidin-1-yl]-3-methyl-2,4-dioxo-1,2,3,4-tetrahydropyrimidin-1-ylmethyl]-benzonitrile is shown in FIG. 1.

According to another embodiment, the present invention is directed to the crystalline form of 2-[6-[3(R)-aminopiperidin-1-yl]-3-methyl-2,4-dioxo-1,2,3,4-tetrahydropyrimidin-1-ylmethyl]-benzonitrile as disclosed above, wherein the infrared spectrum shows peaks at 3358.7+/−2 cm$^{-1}$, 2223.7+/−2 cm$^{-1}$, 1642.2+/−2 cm$^{-1}$, 1433.4+/−2 cm$^{-1}$, 818.4+/−2 cm$^{-1}$ and 771.2+/−2 cm$^{-1}$.

Figure 2:
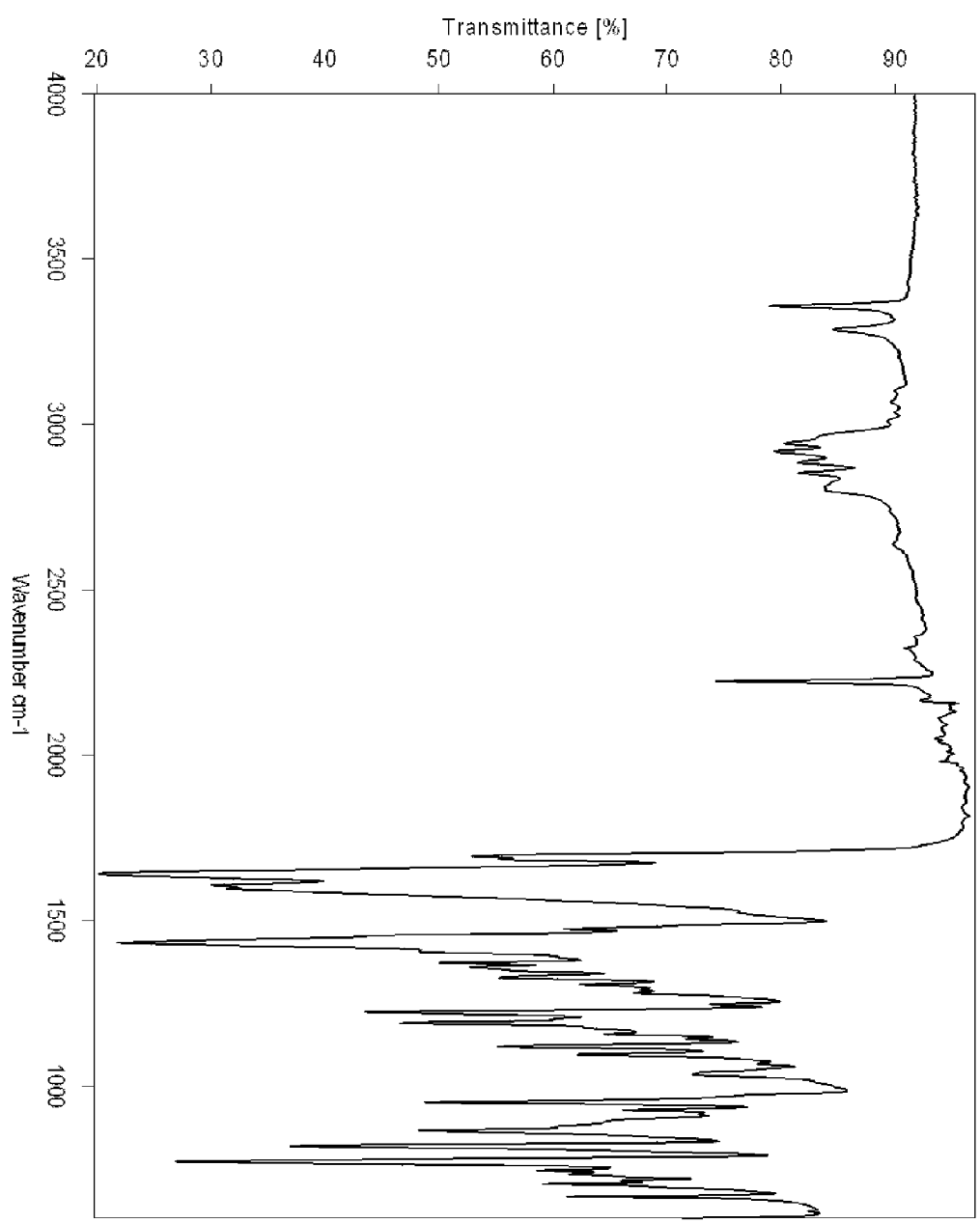
FIG. 2: Infrared spectrum of crystalline alogliptin free base (2-[6-[3(R)-aminopiperidin-1-yl]-3-methyl-2,4-dioxo-1,2,3,4-tetrahydropyrimidin-1-ylmethyl]-benzonitrile) obtained from example 1.

The infrared spectrum of to the crystalline form of 2-[6[3(R)-aminopiperidin-1-yl]-3-methyl-2,4-dioxo-1,2,3,4-tetrahydropyrimidin-1-ylmethyl]-benzonitrile is shown in FIG. 2.

The preferred crystalline 2-[6-[3(R)-aminopiperidin-1-yl]-3-methyl-2,4-dioxo-1,2,3,4-tetrahydropyrimidin-1-ylmethyl]-benzonitrile can be further characterized by a melting point of 127.5° C.±2° C. when measured with a Büchi-545 instrument in automatic mode with a threshold of 40% transmission at a heating rate of 1.0° C./min in Pharmacopoeia mode.

In a preferred embodiment, the invention relates to crystalline 2-[6-[3(R)-aminopiperidin-1-yl]-3-methyl-2,4-dioxo-1,2,3,4-tetrahydropyrimidin-1-ylmethyl]-benzonitrile having a degree of crystallinity of at least 75%, preferably at least 80%.

The crystallization of 2-[6-[3(R)-aminopiperidin-1-yl]-3-methyl-2,4-dioxo-1,2,3,4-tetrahydropyrimidin-1-ylmethyl]-benzonitrile allows to isolate the compound of formula (A) from the reaction mixture in high purity.

The crystalline form of alogliptin free base according to the present invention has the additional advantage that it can be prepared in high purity. Therefore, in a further embodiment, the present invention is directed to the crystalline form of 2-[6-[3(R)-aminopiperidin-1-yl]-3-methyl-2,4-dioxo-1,2,3, 4-tetrahydropyrimidin-1-ylmethyl]-benzonitrile of the invention containing less than 1% of total impurities (area %), preferably from 0.05 area % to 0.5 area % of total impurities, in particular from 0.06 area % to 0.2 area % of total impurities when measured by HPLC in a technically feasible manner, in particular by the method disclosed in the experimental part and disclosed under stability and purity test.

According to a further embodiment, the present invention is therefore directed to the crystalline form of 2-[6-[3(R)-aminopiperidin-1-yl]-3-methyl-2,4-dioxo-1,2,3,4-tetrahydropyrimidin-1-ylmethyl]-benzonitrile as disclosed above, wherein the compound contains less than 1% of total impurities.

In particular, we have found that it is possible according to the present invention to separate off dimeric byproducts of general formula (B) with ease. Thus, according to a further embodiment, the present invention is directed to the crystalline form of 2-[6-[3(R)-aminopiperidin-1-yl]-3-methyl-2,4-dioxo-1,2,3,4-tetrahydropyrimidin-1-ylmethyl]-benzonitrile as disclosed above, wherein the compound contains less than 0.5 area % of dimeric impurity of general formula (B), more preferably from 0.001 area % to 0.2 area % of the dimeric impurity of general formula (B), in particular from 0.002 area % to 0.1 area % of the dimeric impurity of general formula (B), in particular from 0.005 area % to 0.07 area % of the dimeric impurity of general formula (B) when measured by HPLC by the method disclosed in the experimental part (stability and purity test).

According to a further embodiment, the present invention is therefore directed to the crystalline form of 2-[6-[3(R)-aminopiperidin-1-yl]-3-methyl-2,4-dioxo-1,2,3,4-tetrahydropyrimidin-1-ylmethyl]-benzonitrile as disclosed above, wherein the compound contains less than 0.5% of dimeric impurity of general formula (B).

In a further preferred embodiment, the crystalline form of alogliptin free base according to the present invention is essentially free of the dimeric impurity of general formula (B).

Moreover, the crystalline form of alogliptin free base according to the present invention has the additional advantage that it can be used to prepare 2-[6-[3(R)-aminopiperidin-1-yl]-3-methyl-2,4-dioxo-1,2,3,4-tetrahydropyrimidin-1-ylmethyl]-benzonitrile or an acid addition salt thereof, like the benzoate, containing less than 0.5 area % of the dimeric impurity of general formula (B), more preferably from 0.001 area % to 0.2 area % of the dimeric impurity of general formula (B), in particular from 0.002 area % to 0.1 area % of the dimeric impurity of general formula (B), in particular from 0.005 area % to 0.1 area % of the dimeric impurity of general formula (B) when measured by HPLC. According to a further preferred embodiment, the 2-[6-[3(R)-aminopiperidin-1-yl]-3-methyl-2,4-dioxo-1,2,3,4-tetrahydropyrimidin-1-ylmethyl]-benzonitrile or an acid addition salt thereof, like the benzoate, according to the present invention contains the above-mentioned levels of the dimeric impurity of general formula (B) and in particular it is essentially free of the dimeric impurity of general formula (B).

Thus, according to one embodiment, the present invention relates to the use of a crystalline form of 2-[6-[3(R)-aminopiperidin-1-yl]-3-methyl-2,4-dioxo-1,2,3,4-tetrahydropyrimidin-1-ylmethyl]-benzonitrile according to the present invention in the manufacture of an acid addition salt of 2-[6-[3(R)-aminopiperidin-1-yl]-3-methyl-2,4-dioxo-1,2,3,4-tetrahydropyrimidin-1-ylmethyl]-benzonitrile containing less than 0.1% of dimeric impurity of general formula (B).

The present invention is also directed to a process for the preparation of the crystalline form of alogliptin of the invention. According to the present invention, the crystalline form of alogliptin can be obtained by a process comprising the crystallization of alogliptin free base from a suitable solvent.

Thus, the present invention is directed to a process for the preparation of crystalline 2-[6-[3(R)-aminopiperidin-1-yl]-3-methyl-2,4-dioxo-1,2,3,4-tetrahydropyrimidin-1-ylmethyl]-benzonitrile comprising the steps of a) providing a solution of 2-[6-[3(R)-aminopiperidin-1-yl]-3-methyl-2,4-dioxo-1,2,3,4-tetrahydropyrimidin-1-ylmethyl]-benzonitrile in chlorinated hydrocarbon, preferably, wherein the concentration of 2-[6-[3(R)-aminopiperidin-1-yl]-3-methyl-2,4-dioxo-1,2,3,4-tetrahydropyrimidin-1-ylmethyl]-benzonitrile is sufficiently high to allow crystallization of 2-[6-[3(R)-aminopiperidin-1-yl]-3-methyl-2,4-dioxo-1,2,3,4-tetrahydropyrimidin-1-ylmethyl]-benzonitrile;

b) adding an ether, e.g. a symmetrical or unsymmetrical $C_2$-$C_6$ alkylether, in particular an ether selected from diisopropylether, dimethylether and methyl-tert.butylether, or an aliphatic hydrocarbon, in particular pentane, hexane or heptane as an antisolvent in an amount sufficient and at a rate suitable to cause crystallization of 2-[6-[3(R)-aminopiperidin-1-yl]-3-methyl-2,4-dioxo-1,2,3,4-tetrahydropyrimidin-1-ylmethyl]-benzonitrile from the solution of step a); and c) isolating the crystalline form of 2-[6-[3(R)-aminopiperidin-1-yl]-3-methyl-2,4-dioxo-1,2,3,4-tetrahydropyrimidin-1-ylmethyl]-benzonitrile.

In particular, the present invention relates to a process for the preparation of crystalline 2-[6-[3(R)-aminopiperidin-1-yl]-3-methyl-2,4-dioxo-1,2,3,4-tetrahydropyrimidin-1-ylmethyl]-benzonitrile comprising the steps of a) providing a solution of 2-[6-[3(R)-aminopiperidin-1-yl]-3-methyl-2,4-dioxo-1,2,3,4-tetrahydropyrimidin-1-ylmethyl]-benzonitrile in a suitable chlorinated hydrocarbon, wherein the concentration of 2-[6-[3(R)-aminopiperidin-1-yl]-3-methyl-2,4-dioxo-1,2,3,4-tetrahydropyrimidin-1-ylmethyl]-benzonitrile is sufficiently high to allow crystallization of 2-[6-[3(R)-aminopiperidin-1-yl]-3-methyl-2,4-dioxo-1,2,3,4-tetrahydropyrimidin-1-ylmethyl]-benzonitrile;

b) adding an ether, a aliphatic or aromatic hydrocarbon as an antisolvent in an amount sufficient and at a rate suitable to cause crystallization of 2-[6-[3(R)-aminopiperidin-1-yl]-3-methyl-2,4-dioxo-1,2,3,4-tetrahydropyrimidin-1-ylmethyl]-benzonitrile from the solution of step a); and c) isolating the crystalline form of 2-[6-[3(R)-aminopiperidin-1-yl]-3-methyl-2,4-dioxo-1,2,3,4-tetrahydropyrimidin-1-ylmethyl]-benzonitrile.

The process according to the present invention comprises steps a), b), and c).

According to step a), a solution of 2-[6-[3(R)-aminopiperidin-1-yl]-3-methyl-2,4-dioxo-1,2,3,4-tetrahydropyrimidin-1-ylmethyl]-benzonitrile in a chlorinated hydrocarbon, preferably dichloromethane is provided.

According to the present invention, any suitable chlorinated hydrocarbon can be used as solvent, in particular dichloromethane. According to step b), a suitable antisolvent is added selected from ethers and aliphatic or aromatic hydrocarbons. According to the present invention, any suitable ether or aliphatic or aromatic hydrocarbon can be used.

A solution of 2-[6-[3(R)-aminopiperidin-1-yl]-3-methyl-2,4-dioxo-1,2,3,4-tetrahydropyrimidin-1-ylmethyl]-benzonitrile may be provided by extraction of an aqueous solution or a solution of the compound of general formula (A) in a mixture of water and the organic solvent origination e.g. from a reaction mixture e.g. from the reaction of 2-(6-chloro-3-methyl-2,4-dioxo-3,4-dihydro-2-H-pyrimidin-1-ylmethyl)benzonitrile and (R)-3-amino-piperidine or a salt thereof with a chlorinated hydrocarbon, preferably di-chloromethane In a preferred embodiment 2-(6-chloro-3-methyl-2,4-dioxo-3,4-dihydro-2-H-pyrimidin-1-ylmethyl)benzonitrile and (R)-3-amino-piperidine or a salt thereof, e.g. (R)-3-amino-piperidine dihydrochloride, are reacted in a mixture of a $C_1$-$C_4$ alcohol and water, preferable isopropanol and water, most preferably in a ratio of about 10:1(v/v) to 2:1(v/v), preferable in a ration of about 3:1(v/v) to 5:1(v/v), more preferably of about 4:1 (v/v) in presence of a base, preferably an alkali carbonate or an alkali bicarbonate, e.g. Na—$HCO_3$ or $Na_2CO_3$.

Preferably, the reaction mixture is then concentrated in vacuo and the alkaline mixture is participated in a mixture of water and chlorinated hydrocarbon, preferably dichloromethane The mixture is then preferable filtered and the layers are separated. The aqueous alkaline layer is optionally additionally extracted with a chlorinated hydrocarbon, preferably dichloromethane. The product containing organic phase is optionally dried with aid of a drying agent. The organic phase is preferably filtered to remove possible insoluble material or drying agents and is then concentrated. The concentration step is performed to a concentration of 2-[6-[3(R)-aminopiperidin-1-yl]-3-methyl-2,4-dioxo-1,2,3,4-tetrahydropyrimidin-1-ylmethyl]-benzonitrile which is sufficiently high to allow crystallization, for example a residue containing about at least 50% (w/w) of product is preferred, in particular a residue containing from 70% to 90% (w/w) of product.

Alternatively a solution of 2-[6-[3(R)-aminopiperidin-1-yl]-3-methyl-2,4-dioxo-1,2,3,4-tetrahydropyrimidin-1-ylmethyl]-benzonitrile may be provided by dissolving an oil or solid compound of general formula (A) in a chlorinated hydrocarbon, preferably di-chloromethane.

To the solution is then added slowly the antisolvent ether, in particular a symmetrical or unsymmetrical $C_2$-$C_6$ alkylether, e.g. diisopropylether, dimethylether, methyl-ert.butylether, or the antisolvent aliphatic hydrocarbon, in particular a linear aliphatic hydrocarbon, e.g. pentane, hexane or heptane or mixtures thereof, in a rate to effect crystallization of 2-[6-[3(R)-aminopiperidin-1-yl]-3-methyl-2,4-dioxo-1,2,3,4-tetrahydropyrimidin-1-ylmethyl]-benzonitrile with stirring, in particular the dropwise, linear addition is effected within 5 min to several hours, preferable within about 15 min to 1 hour. Preferred solvent/antisolvent systems are dichloromethane as a solvent and diisoprpylether, methyl.-tert. butylether or hexane or heptane or mixtures thereof as antisolvents. The solution containing 2-[6-[3(R)-aminopiperidin-1-yl]-3-methyl-2,4-dioxo-1,2,3,4-tetrahydropyrimidin-1-ylmethyl]-benzonitrile may be dried before the crystallization step, however the drying step is not critical. A suitable concentration of 2-[6-[3(R)-aminopiperidin-1-yl]-3-methyl-2,4-dioxo-1,2,3,4-tetrahydropyrimidin-1-ylmethyl]-benzonitrile for the crystallization in high yield is e.g. a solution containing at least 20% (w/w) of product, e.g a concentration of at least 50% (w/w) of product, e.g. 70% to 90% of product is preferred.

Suitable solvents according to the present invention include halogenated hydrocarbons, like dichloromethane.

According to step b) of the process of the present invention, 2-[6-[3(R)-aminopiperidin-1-yl]-3-methyl-2,4-dioxo-1,2,3,4-tetrahydropyrimidin-1-ylmethyl]-benzonitrile is crystallized from the solution.

The temperature of the crystallization process is not critical, e.g. temperatures from about 0° C. to the boiling point of the solvent or solvent mixture may be applied.

Crystallization may then be induced by cooling of the solution. Seeds may be present in the crystallization procedure. The cooling procedure may be performed by cooling the solution or suspension, preferably to a temperature of about −20° C. to about 10° C., more preferably to a temperature of between about −20° C. and about 0° C. Preferably cooling is performed slowly, e.g. within several hours or e.g. within approximately 10 to 120 min.

According to a further embodiment, the crystallization may be induced by addition of an antisolvent as disclosed above, for example an ether, e.g. a symmetrical or unsymmetrical $C_2$-$C_6$ alkylether, e.g. diisopropylether, dimethylether, methyl-tert.butylether or hexane or heptane. Optionally seeds may be added to induce crystallization.

The amount of antisolvent used is from about 2 to 100 times by volume the amount of solvent present, preferable an amount of 5 to 20 times by volume the amount of solvent present.

Preferably, to the concentrated solution the antisolvent is added at a temperature from about ambient temperature to about 40° C., e.g. from about 15° C. to 40° C. while stirring. After addition of the antisolvent, the mixture may be cooled e.g. to about 5° to −20° C., e.g. to about 5° C. to 0° C. in an ice bath to complete crystallization. Optionally additional antisolvent may be added to the suspension containing the crystalline product.

Therefore, according to one embodiment, the present invention is directed to a process for the preparation of crystalline 2-[6-[3(R)-aminopiperidin-1-yl]-3-methyl-2,4-dioxo-1,2,3,4-tetrahydropyrimidin-1-ylmethyl]-benzonitrile as disclosed above, wherein step b) comprises adding an antisolvent to the solution to effect crystallization.

According to a further embodiment, the present invention is directed to a process for the preparation of crystalline 2-[6-[3(R)-aminopiperidin-1-yl]-3-methyl-2,4-dioxo-1,2,3,4-tetrahydropyrimidin-1-ylmethyl]-benzonitrile as disclosed above, wherein the antisolvent is selected from the group of ethers and aliphatic hydrocarbons.

Therefore, according to a further embodiment, the present invention is directed to the process for the preparation of crystalline 2-[6-[3(R)-aminopiperidin-1-yl]-3-methyl-2,4-dioxo-1,2,3,4-tetrahydropyrimidin-1-ylmethyl]-benzonitrile as disclosed above, wherein the ether is selected from a symmetrical or unsymmetrical $C_2$-$C_6$ alkylether and the aliphatic hydrocarbon from pentane or hexane.

According to the present invention it is also possible to combine the above mentioned methods to induce crystallization.

According to step c), the crystalline form of 2-[6-[3(R)-aminopiperidin-1-yl]-3-methyl-2, 4-dioxo-1,2,3,4-tetrahydropyrimidin-1-ylmethyl]-benzonitrile is isolated.

According to the present invention, the crystalline product can be isolated by conventional methods, e.g. filtration by suction. The crystalline product may be dried by conventional methods, e.g. air drying, drying with under a flow of nitrogen, or vaccum drying.

The process of the present invention may also comprise further steps.

2-[6-[3(R)-Aminopiperidin-1-yl]-3-methyl-2,4-dioxo-1,2,3,4-tetrahydropyrimidin-1-ylmethyl]-benzonitrile of high quality easily may be converted to the desired acid addition salt, e.g. to a desired pharmaceutically acceptable salt, e.g. to a benzoate by known methods.

Thus, according to a further embodiment, the present invention is directed to the use of the crystalline form of 2-[6-[3(R)-aminopiperidin-1-yl]-3-methyl-2,4-dioxo-1,2,3,4-tetrahydropyrimidin-1-ylmethyl]-benzonitrile in the manufacture of an addition salt of 2-[6-[3(R)-aminopiperidin-1-yl]-3-methyl-2,4-dioxo-1,2,3,4-tetrahydropyrimidin-1-ylmethyl]-benzonitrile.

According to another embodiment, the present invention is directed to the use of the crystalline form of 2-[6-[3(R)-aminopiperidin-1-yl]-3-methyl-2,4-dioxo-1,2,3,4-tetrahydropyrimidin-1-ylmethyl]-benzonitrile in the manufacture of a pharmaceutical composition.

By using the crystalline form of alogliptin free base according to the present invention, it is possible to obtain addition salts, e.g. the benzoate, of alogliptin containing only small amounts of impurities, in particular only small amounts of the dimeric impurities of general formula (B).

Thus, the present invention is also directed to 2-[6-[3(R)-Aminopiperidin-1-yl]-3-methyl-2,4-dioxo-1,2,3,4-tetrahydropyrimidin-1-ylmethyl]-benzonitrile benzoate containing less than 0.1 area % of dimeric impurity of general formula (B), e.g less than 0.05 area %, e.g. less than 0.02%, in particular from 0.001 area % to 0.2 area % of the dimeric impurity of general formula (B), in particular from 0.002 area % to 0.1 area % of the dimeric impurity of general formula (B), in particular from 0.005 area % to 0.1 area %, from 0.005 area % to 0.08 area %, from 0.005 area % to 0.06 area %, from 0.005 area % to 0.04 area % of the dimeric impurity of general formula (B) when measured by HPLC.

Thus, the present invention is directed to 2-[6-[3(R)-Aminopiperidin-1-yl]-3-methyl-2,4-dioxo-1,2,3,4-tetrahydropyrimidin-1-ylmethyl]-benzonitrile benzoate containing less than 0.1% of dimeric impurity of general formula (B).

Finally, the present invention is directed to a pharmaceutical composition comprising the crystalline form of 2-[6-[3(R)-aminopiperidin-1-yl]-3-methyl-2,4-dioxo-1,2,3,4-tetrahydropyrimidin-1-ylmethyl]-benzonitrile, in particular for the treatment of diabetes.

The present invention is further illustrated by the following examples.

EXAMPLES

The X-ray powder diffraction pattern (XRPD) was collected on an X-ray powder diffractometer D-8 (AXS-BRUKER):

Theta-theta-goniometer, sample changer
Target: copper, $K_{\alpha 1}+K_{\alpha 2\lambda}=1.5406$ A
Parallel beam optics (receiving soller-slit: 0.07 mm)
Scintillation counter, standard sample holder
Data collection: 40 kV, 40 mA, 2-40° theta/2-theta, 0.01 steps, 2 seconds
External d-spacing standards
NIST SRM 640A (Silicon powder)

The % crystallinity of of an obtained product was determined based on powder X-ray diffractograms. The % cyrstallinity was calculated with the formula % crystallinity=100*E/(E+F)

E=peak area obtained by integration of the peaks in the diffractogram, representing the amount of crystalline material F=area between the peaks and the background, representing the amount of non-crystalline material Area calculations were performed between 5-40° 2 Theta. The lowest intensity value found in this interval was defined as the constant background value and a rectangle with the area "constant background value"*35(1° 2 Theta was given a numerical value of 1 for area calculations) was substracted from the area F for the interval between 5 and 40° 2 Theta.

The Infrared spectrum (IR) was collected on an MKII Golden Gate™ Single Reflection Diamond ATR (attenuated total reflection) cell with a Bruker Tensor 27 FTIR spectrometer with 4 cm$^{-1}$ resolution at ambient conditions. To collect a spectrum a spatula tip of the sample was applied to the surface of the diamond in powder form. Then the sample was pressed onto the diamond with a sapphire anvil and the spectrum was recorded. A spectrum of the clean diamond was used as background spectrum. A typical precision of the wave number values is in the range of about ±2 cm$^{-1}$. Thus, an infrared peak that appears at 1716 cm$^{-1}$ can appear between 1714 and 1718 cm$^{-1}$ on most infrared spectrometers under standard conditions.

Example 1

2-[6-[3(R)-Aminopiperidin-1-yl]-3-methyl-2,4-dioxo-1,2,3,4-tetrahydropyrimidin-c1-ylmethyl]-benzonitrile A mixture of (R)-3-aminopiperidine×2HCl (0.70 g, 4.0 mmol) and NaHCO$_3$ (1.70 g, 20.2 mmol) and H$_2$O (1 ml) was stirred for 5 minutes. 2-Propanol (4 ml) and 6-chloro-2-(2-cyanobenzyl)-3-methyluracil (0.93 g, 3.4 mmol) were then added to the aqueous mixture. The mixture was then stirred at a bath temperature of about 70° C. for 40 hours. Most of 2-propanol was then removed from the reaction mixture by distillation in vacuo.

To the residue was added CH$_2$Cl$_2$ (25 ml) and H$_2$O (15 ml). The layers were separated and the aqueous layer was extracted with CH$_2$Cl$_2$ (15 ml). The combined organic layers were extracted twice with 1M hydrochloric acid (25 and 10 ml). The acidic aqueous phase was washed with CH$_2$Cl$_2$ (5 ml), pH was adjusted to approximately 7.5 by addition of solid NaHCO$_3$ with stirring. The aqueous solution was then extracted twice with CH$_2$Cl$_2$ (25 and 15 ml). The organic layer was dried with anhydrous MgSO$_4$, filtered and concentrated to a volume of about 2 ml. To the residue was added diethyl ether (5 ml) with stirring within about 30 min and the mixture was stirred at ambient temperature (about 22° C.) for further 4 hours The crystals were isolated by filtration and dried in vacuo overnight.

Yield: 0.80 g $^1$H NMR (CDCl$_3$, 300 MHz): δ 1.21 (m, 1H), 1.40 (br s, 2H), 1.62 (m, 1H), 1.76 (m, 1H), 1.93 (m, 1H), 2.38 (t, 1H), 2.59 (t, 1H), 2.91 (m, 2H), 3.02 (m, 1H), 3.31 (s, 3H), 5.29 (AB, J=16 Hz, 2H), 5.37 (s, 1H), 7.13 (d, J=8 Hz, 1H), 7.37 (t, J=8 Hz, 1H), 7.55 (Td, J=8 Hz, J=1 Hz, 1H), 7.67 (Dd, J=8 Hz, J=1 Hz, 1H) ppm.

HPLC purity: 99.8%; dimeric impurity of general formula (B): 0.06 area % (HPLC conditions see stability and purity test.)

% defines area % (peak area of the impurity divided by the total area of peaks times 100 in the HPLC chromatogram from 0 to 20 min runtime, wherein an apparent injection peak, if at all present, is ignored.)

Example 2

2-[6-[3(R)-Aminopiperidin-1-yl]-3-methyl-2,4-dioxo-1,2,3,4-tetrahydropyrimidin-c1-ylmethyl]-benzonitrile A mixture of (R)-3-aminopiperidine×2HCl (3.00 g, 17.3 mmol) and NaHCO$_3$ (7.28 g, 86.7 mmol) was stirred in H$_2$O (4 ml) at 20° C. for 5 minutes. 2-Propanol (16 ml) and 6-chloro-2-(2-cyanobenzyl)-3-methyluracil (4.30 g, 15.6 mmol) were added to the aqueous mixture. The reaction mixture was stirred at a bath temperature of 70° C. for 89 hours. Most of 2-propanol was removed from the mixture in vacuo. To the residue was added CH$_2$Cl$_2$ (100 ml) and H$_2$O (50 ml). The mixture was filtered, layers were separated and the aqueous layer was washed with CH$_2$Cl$_2$ (50 ml). The organic layers were combined and extracted twice with 1M HCl (100 und 50 ml). The aqueous solution was extracted with CH$_2$Cl$_2$ (20 ml) and neutralized with solid NaHCO$_3$ while stirring. The solution was then extracted twice with CH$_2$Cl$_2$ (100 und 50 ml). The organic solution was filtered and concentrated in vacuo. To the oily residue was added diisopropyl ether (20 ml) at ambient temperature (about 20° C.) with agitation within approximately 5 min and the product started to crystallize while stirring. The suspension was stirred for another 2 hours and the crystals were then isolated by filtration and dried in vacuo overnight.

Yield: 3.55 g

Example 3

2-[6-[3(R)-Aminopiperidin-1-yl]-3-methyl-2,4-dioxo-1,2,3,4-tetrahydropyrimidin-c1-ylmethyl]-benzonitrile A mixture of (R)-3-aminopiperidin.2HCl (0.70 g, 4.0 mmol) and NaHCO$_3$ (1.70 g, 20.2 mmol) and H$_2$O (1 ml) was stirred for 5 minutes. 2-Propanol (4 ml) und 6-chloro-2-(2-cyanobenzyl)-3-methyluracil (0.93 g, 3.4 mmol) were then added to the aqueous mixture. The mixture was then stirred at a bath temperature of about 70° C. for 40 hours. Most of 2-propanol was then removed from the reaction mixture by distillation in vacuo. To the residue was added CH$_2$Cl$_2$ (25 ml) and H$_2$O (15 ml). The layers were separated and the aqueous layer was extracted with CH$_2$Cl$_2$ (15 ml). The combined organic layers were extracted twice with 1M hydrochloric acid (25 and 10 ml). The acidic aqueous phase was washed with CH$_2$Cl$_2$ (5 ml), pH was adjusted to approximately 7.5 by addition of solid NaHCO$_3$ with stirring. The aqueous solution was then extracted twice with CH$_2$Cl$_2$ (25 und 15 ml). The organic layer was dried with anhydrous MgSO$_4$, filtered and concentrated to a volume of about 2 ml. To the residue was added n-hexane (5 ml) at room temperature within approximately 20 min with stirring. Crystals precipitated from the solution and the suspension was stirred at ambient temperature (about 22° C.) for 4 hours. The crystals were then isolated by filtration, washed with n-hexane (5 ml) and dried in vacuo overnight.

Yield: 0.87 g
Water content (KF): 0.25%

Example 4

2-[6-[3(R)-Aminopiperidin-1-yl]-3-methyl-2,4-dioxo-1,2,3,4-tetrahydropyrimidin-c1-ylmethyl]-benzonitrile benzoate A mixture of 3.40 g of 2-[6-[3(R)-aminopiperidin-1-yl]-3-methyl-2,4-dioxo-1,2,3,4-tetrahydropyrimidin-c1-ylmethyl]-benzonitrile and 1.22 g of benzoic acid was stirred in 200 ml of ethanol at 70° C. for 1 hour. The solution was allowed to cool to ambient temperature and was then kept in the fridge for approximately 36 hours.

The crystals were isolated by filtration and dried in vacuo at 50° C. for 8 hours. HPLC purity: 99.9%, dimeric impurity of general formula (B): not detected, that is its level was at least below 0.05 area %.

Stability and Purity Test:
HPLC conditions:
Apparatus: Agilent 11 Series
Column: YMC-Pro C18; 150×4,6 mm, S-5 μm, 120A
Eluent: mobile phase A: 3.884 g of amidosulfonic acid in 1000 g of water; mobile phase B: 3.884 g of amidosulfonic acid in 250 g of water and 588 g of acetonitrile.
Measurement at a wavelength of 220 nm; injection volume 7 μl, oven temperature 40° C., Flow 1.0 ml/min
Sample preparation: approximately 10 mg of a sample of the crystalline form of alogliptin free base are dissolved in 10 ml of acetonitrile and the solution is filled up to 25 ml with water
Run time 20 min
Gradient:

| t (min) | % A | % B |
|---|---|---|
| 0 | 70 | 30 |
| 14 | 0 | 100 |
| 19 | 0 | 100 |
| 20 | 70 | 30 |

The invention claimed is:

1. A crystalline form of 2-[6-[3(R)-aminopiperidin-1-yl]-3-methyl-2,4-dioxo-1,2,3,4-tetrahydropyrimidin-1-ylmethyl]-benzonitrile wherein the x-ray powder diffraction comprises peaks at 2-theta of 10.9°±0.2°, 12.5°±0.2°, 18.0°±0.2°, 19.0°±0.2°, 21.8°±0.2°.

2. The crystalline form of 2-[6-[3(R)-aminopiperidin-1-yl]-3-methyl-2,4-dioxo-1,2,3,4-tetrahydropyrimidin-1-ylmethyl]-benzonitrile according to claim 1, wherein the crystalline form is an anhydrous form containing less than 1.6% of water when stored at 25° C. and 90% relative humidity.

3. The crystalline form of 2-[6-[3(R)-aminopiperidin-1-yl]-3-methyl-2,4-dioxo-1,2,3,4-tetrahydropyrimidin-1-ylmethyl]-benzonitrile according to claim 1, wherein the infrared spectrum shows peaks at 3358.7+/−2 $cm^{-1}$, 2223.7+/−2 $cm^{-1}$, 1642.2+/−2 $cm^{-1}$, 1433.4+/−2 $cm^{-1}$, 818.4+/−2 $cm^{-1}$ and 771.2+/−2 $cm^{-1}$.

4. The crystalline form of 2-[6-[3(R)-aminopiperidin-1-yl]-3-methyl-2,4-dioxo-1,2,3,4-tetrahydropyrimidin-1-ylmethyl]-benzonitrile according to claim 1, wherein the compound contains less than 1% of total impurities.

5. The crystalline form of 2-[6-[3(R)-aminopiperidin-1-yl]-3-methyl-2,4-dioxo-1,2,3,4-tetrahydropyrimidin-1-ylmethyl]-benzonitrile according to claim 1, wherein the compound contains less than 0.5% of dimeric impurity of formula (B):

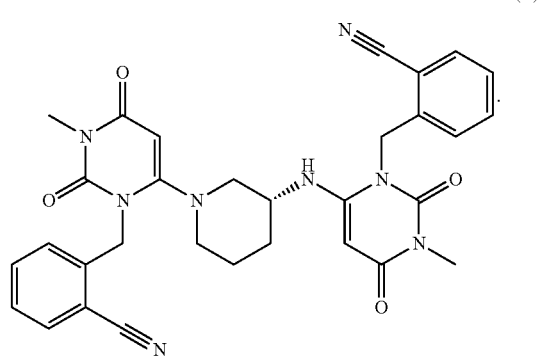

(B)

* * * * *